United States Patent
Wolff et al.

(10) Patent No.: US 6,180,784 B1
(45) Date of Patent: *Jan. 30, 2001

(54) PROCESS OF TRANSFECTING A CELL WITH A POLYNUCLEOTIDE MIXED WITH AN AMPHIPATHIC COMPOUND AND A DNA-BINDING PROTEIN

(75) Inventors: Jon A. Wolff; James E. Hagstrom; Vladimir G. Budker, all of Madison, WI (US); Jeffery Fritz, Nashville, TN (US)

(73) Assignee: Mirus Corporation, Madison, WI (US)

(*) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/020,566

(22) Filed: Jan. 17, 1998

Related U.S. Application Data

(62) Division of application No. 08/530,598, filed on Sep. 19, 1995, now Pat. No. 5,744,335.

(51) Int. Cl.[7] ............. C07D 255/02; C07D 241/04; C07C 21/00
(52) U.S. Cl. ............. 540/474; 544/402; 564/509; 564/512
(58) Field of Search ............. 564/509, 512; 540/474; 544/402

(56) References Cited

U.S. PATENT DOCUMENTS 5,091,576 * 2/1992 Bergeron ............. 564/367

OTHER PUBLICATIONS

Guo et al, CA 111:28531, 1989.*
Shinozaki et al, CA 111: 97286, 1989.*
Thomas et al, CA 116:173167, 1992.*
CA 59:14963e, 1959.*
CA 63: 8518h, 1963.*
Fakhretdinov et al, CA 108: 56095.*

* cited by examiner

Primary Examiner—Deborah C. Lambkin
(74) Attorney, Agent, or Firm—Mark K. Johnson

(57) ABSTRACT

The present invention provides a process of transfecting a cell with a polynucleotide mixed with one or more amphipathic compounds and an effective amount of a DNA-binding protein. Exemplary and preferred DNA-binding proteins are H1, H2A, and H2B. Exemplary and preferred amphipathic compounds are cationic amphipathic compounds.

8 Claims, No Drawings

PROCESS OF TRANSFECTING A CELL WITH A POLYNUCLEOTIDE MIXED WITH AN AMPHIPATHIC COMPOUND AND A DNA-BINDING PROTEIN

CROSS-REFERENCE TO RELATED APPLICATIONS

This application is a divisional of application Ser. No. 08/530,598 filed Sep. 9, 1995 U.S. Pat. No. 5,744,335.

FIELD OF THE INVENTION

This invention generally relates to techniques for transferring genes into mammalian cells. The method provides a method for transfecting cells with high efficiency and low cellular toxicity.

BACKGROUND OF THE INVENTION

Despite the great promise of gene therapy, there remains to be solved the challenging problem of efficiently transferring and stably expressing transgenes in appropriate tissues. This problem has recently been termed the "vector void" (Hodgson, C P. Bio/Technol. 1995;13:222–225). After the description of DOTMA (N-[1-(2,3-dioleyloxy)propyl]-N,N,N-trimethylammonium chloride) (Felgner, P L, Gadek, T R, Holm, M, et al. Proc. Natl. Acad. Sci. USA. 1987;84:74137417), a plethora of cationic lipids have been synthesized. Basically, all the cationic lipids are amphipathic compounds that contain a hydrophobic domain, a spacer, and positively-charged amine(s). The cationic lipids are mixed with a fusogenic lipid such as DOPE (dioleoyl phosphatidyl ethanolamine) to form liposomes. The cationic liposomes are then mixed with plasmid DNA and the binary complex of the DNA and liposomes are then applied to cells in a tissue culture dish. The ease of mixing the plasmid DNA with the cationic liposome formulation, the ability of the cationic lipids to complex with DNA and the relative high levels of transfection efficiency has led to he increasing use of these formulations. However, these cationic lipid formulations can also be toxic to the cells in culture (Gao, X and Huang, L. Biochem. Biophys. Res. Com. 1991;179:280–285) (Leventis, R and Silvius, J R. Biochim. et Biophys. Acta 1990;1023:124–132). Although, LipofectAMINE can transfect many cell types more efficiently than other types of cationic lipid formulations (Harms, J S and Splitter, G A. Focus 1994;17:34–35), it also has greater toxicity (Hawley-Nelson, P, Ciccarone, V and Jessee, J. Focus 1993;15:73–79) (Ciccarone, V, Hawley-Nelson, P and Jessee, J. Focus 1993;15:80–83). If the transfection method is toxic to cells, then this would reduce its applicability for gene therapy. Cellular toxicity would also reduce its applicability to the study of genes since the cells would be in an altered state and it may be difficult to differentiate an effect of the transfection reagent from expression of the foreign gene.

Accordingly, there is a need for a means of transfecting cells with great efficiency and little toxicity. In addition, given the vector void for gene therapy, there is a need for new types of methods to transfer genes into mammalian cells.

SUMMARY OF THE INVENTION

The present invention provides an enhancement of gene transfer into cells using a ternary complex of DNA, amphipathic compounds, and a DNA-binding protein. Cultured cells exposed to these ternary complexes expressed foreign genes at very high levels and with minimal cellular toxicity. Further, the use of a DNA-binding protein and novel amphipathic compounds together increased gene transfer efficiency by several orders of magnitude.

In one aspect, the present invention provides a process of transfecting a cell with DNA comprising exposing the cell to the DNA mixed with amphipathic compounds and an effective amount of a DNA-binding protein.

A preferred DNA-binding protein is a histone such as H1, H2A, or H2B. Natural DNA binding proteins such as histone also have several advantages over polycationic compounds such as polylysine. Human H1 histone protein is not immunogenic and does not induce anaphylaxis. Polylysine induces anaphylactic shock and is very immunogenic.

In one preferred embodiment, the DNA-binding protein is linked to a nuclear localization signal. A recombinant histone (NLS-H1) containing both the SV40 large T antigen nuclear localization signal and the C-terminal domain of human histone H1 was produced in bacteria. NIH3T3 or COS-7 cells transfected with NLS-H1 plasmid DNA-Lipofectin complexes expressed at least 20 times more liuciferase or had at least 2.5 times more B-galactosidase positive cells than those transfected with plasmid DNA-lipofectin complexes alone. Foreign gene expression was also improved by other DNA-binding proteins and cationic lipid formulations, but the greatest enhancement in foreign gene expression was obtained with complexes containing either NLS-H1 or calf-thymus histone H1.

A variety of amphipathic compounds can be used in conjunction with a DNA binding protein such as histone protein to mediate the transfer of the plasmid DNA into the cell. A preferred embodiment is amphipathic compounds that are cationic. The cationic amphipathic compound can be a non-natural polyamine wherein one or more of the amines is bound to at least one hydrophobic moiety wherein the hyudrophobic moiety comprises a C6–C24 alkane, C6–C24 alkene, sterol, steroid, lipid, fatty acid or hydrophobic hormone. The amphipathic compounds may or may not form liposomes. Several novel amphipathic cationic compounds are described. These include compounds with the following structures:

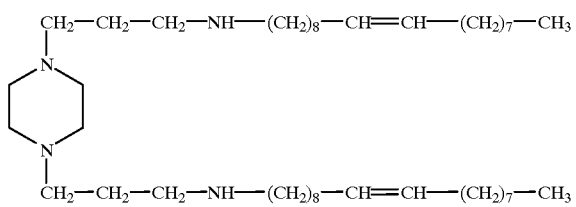

and
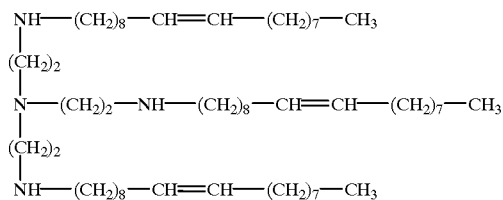
and
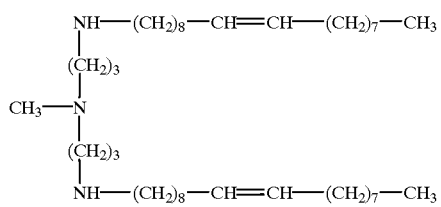
and
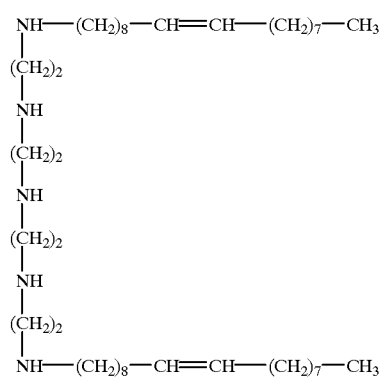
and
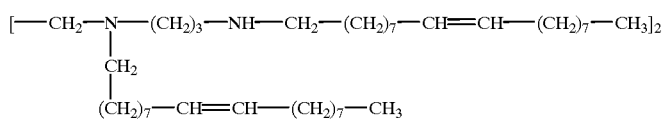
and
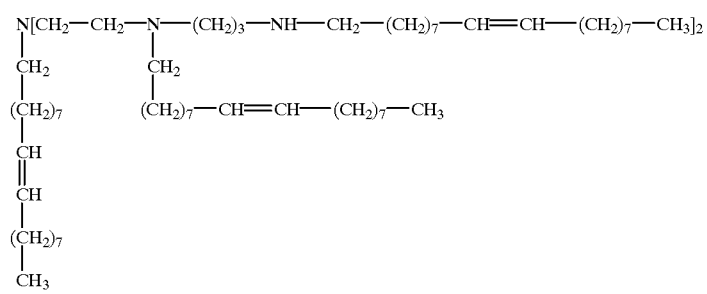
and
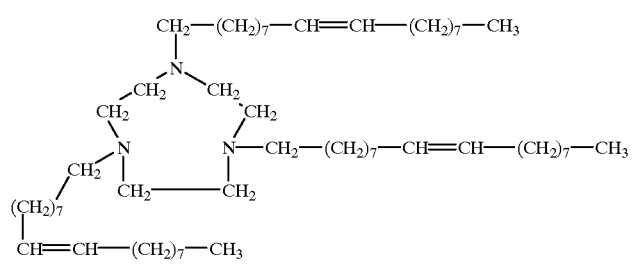
and -continued

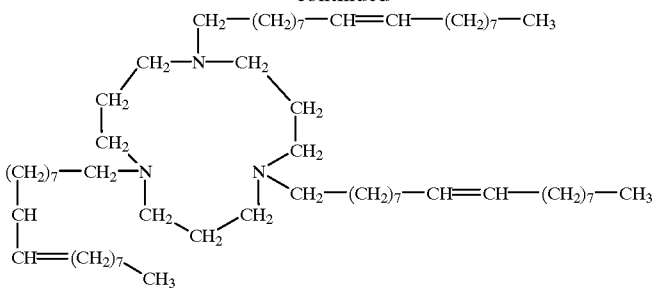

In contrast to the use of previously described cationic liposomes, most of the novel amphipathic cationic compounds described above do not efficiently mediate the transfer of genes into cells when used alone. However, the use of histone proteins with these novel amphipathic cationic compounds enable the efficient gene transfer into a variety of mammalian cells with minimal cellular toxicity. Therefore, the use of histone proteins expands the range and types of cationic lipids that can be used for gene transfer.

Histone H1-plasmid DNA-cationic lipid complexes showed less cytotoxicity and were internalized by a greater number of cells than plasmid DNA-cationic lipid complexes. Thus, histone binding to plasmid DNA prior to the addition of cationic amphipathic compounds improved cellular uptake and transient foreign gene expression while reducing the cellular toxicity associated with cationic-lipid mediated gene transfer.

DETAILED DESCRIPTION

The present invention includes a process of transfecting a polynucleotide into a cell for expression by associating a selected cell with an amphipathic compound, an effective amount of a polynucleotide-binding protein and a selected polynucleotide, in solution. The term "transfecting" means that a polynucleotide becomes associated with a selected cell. The polynucleotide can be on the membrane of the cell or inside the cytoplasm, nucleus, or other organeile of the cell. Other terms sometimes used interchangeably with transfecting include "delivering" or "transferring" to a cell and "transforming" a cell.

The polynucleotide is delivered to the cell by associating the cell with one or more amphipathic compounds along with a polynucleotide-binding protein in a solution. The term "associating" means to put in communication with or to place in close proximity. The term "polynucleotide" is a term of art that refers to a string of at least two base-sugar-phosphate combinations. Nucleotides are the monomeric units of nucleic acid polymers. The term includes deoxyribonucleic acid (DNA) and ribonucleic acid (RNA) in the form of an oligonucleotide, messenger RNA, anti-sense, plasmid DNA, parts of a plasmid DNA or genetic material derived from a virus. The selected cell can be a mammalian cell that is within the tissue in situ; the cell could also be removed and maintained in tissue culture in a primary, secondary, immortalized or transformed state.

The amphipathic compound is a linear molecule with a polar first end causing that end to be hydrophilic (water-soluble); the second end is nonpolar and therefore hydrophobic (water-insoluble). The amphipathic compound can be cationic or incoporated into a liposome that is cationic or anionic. In one embodiment, the amphipathic compound is a non-natural polyamine. "Non-natural", in this application, means that, for example, the compound is not found in living matter. As contrasted with "natural" which in this application refers to a compound that is derived from animal or plant tissue directly or by recombinant means.

The polynucleotide-binding protein is a protein that can be used in an effective amount in its natural form or modified for this process. An "effective amount" of the polynucleotide-binding protein is an amount that will allow transfection to occur. In a preferred embodiment, the polynucleotide-binding protein is a DNA-binding protein which is isolated from an animal tissue, such as calf thymus or produced in recombinant form from $E.\ coli$. The DNA-binding protein associates with DNA under conditions described in this application and forms a complex with DNA having a high binding constant. Preferably, the DNA-binding protein is cationic (net positive charge) such as a histone protein. H1 histone protein is the preferred histone type. In yet another preferred embodiment, histone H1 protein is used as a DNA-binding protein and one of the compounds #4, #11, #16, #17, #20, #21, #23, #30, and #32 is used for the amphipathic compound in the form of liposomes. This invention is of particular use for the delivery of a polynucleotide when one wants to study the polynucleotide's effect on a cell. The polynucleotide could also be used to produce a change in a cell that can be therapeutic. This change can be effected when the cell is transplanted back into the animal or person. The delivered polynucleotide could also produce a therapeutic protein or RNA that is then delivered to the animal or person apart from the cell. Transfections are also done to produce viruses or viral vectors that are studied or used for therapeutic, gene therapy purposes. The delivery of polynucleotides or genetic material for therapeutic purposes is commonly called "gene therapy".

1. Preparation of Cells

The cell can be a mammalian cell that is maintained in tissue culture such as cell lines that are immortalized or transformed. These include a number of cell lines that can be obtained from American Tissue Culture Collection (Bethesda) such as 3T3 mouse fibroblasts, Rat1 rat fibroblasts, CV-1 monkey kidney cells, COS (monkey kidney) cells, 293, HeLa (human cervical carcinoma) cells, or HepG2 (human) hepatocytes.

The mammalian cell can be primary or secondary which means that it has been maintained in culture for a relatively short time after being obtained from an animal tissue. These include primary liver cells or primary muscle cells. The cells within the tissue are separated by mincing and digestion with enzymes such as trypsin or collagenases that destroy the extracellular matrix. Tissues consist of several different cell types and purifications methods such as gradient centrifugation or antibody sorting can be used to obtain purified amounts of the preferred cell type. For example, primary myoblasts are separated from contaminating fibroblasts using Percoll (Sigma) gradient centrifugation.

Both the primary cells and cell lines are grown (cultured) in tissue culture media such as Dulbeco's Modified MEM media (D-MEM, Life Technologies, Inc.) supplemented with 10% fetal calf serum (Hyclone, Logan, Utah) for the 3T3 and HepG2 cells. The cultures are maintained in a humidified atmosphere of 5% CO2 in air at 37 degrees C. The cells are seeded in 6-well plates (35 mm-in diameter culture dishes) 24 h before the transfection at 40–60% confluence.

2. Preparation of Polynucleotides

The polynucleotide can be a deoxyribonucleic acid (DNA) in the form of an oligonucleotide, anti-sense, plasmid DNA, parts of a plasmid DNA or genetic material derived from a virus. The polynucleotide can also be a ribonucleic acid (RNA). The RNA can be produced using synthetic chemical techniques (RNA in the form of an oligonucleotide) or biochemically using a RNA polymerase such T7 RNA polymerase (G1) and a DNA template containing the cognate T7 promoter (Deng, H and Wolff, J A. Self-amplifying expression from the T7 promoter in 3T3 mouse fibroblasts. Gene 1994;143:245–249).

In one preferred embodiment, the exogenous genetic construction is a plasmid DNA that consists of DNA from another organism, of the same or different species. The plasmid DNA constructions normally include a coding sequence for a transcription product or a protein of interest, together with flanking regulatory sequences effective to cause the expression of the protein in the transfected cells. Examples of flanking regulatory sequences are a promoter sequence sufficient to initiate transcription and a terminator sequence sufficient to terminate the gene product, by termination of transcription or translation. Suitable transcriptional or translational enhancers can be included in the exogenous gene construct to further assist the efficiency of the overall transfection process and expression of the protein in the transfected cells.

A marker or reporter gene encodes a gene product which can be easily assayed, such as a the firefly luciferase. The presence of the product of the marker gene indicates that the cell is transfected and the amount of the product indicates how efficient the transfection process. The firefly luciferase reporter gene was used in most of our studies to determine the efficiency of DNA transfer quantitatively. The previously described, plasmid DNA pBS.CMVLux was used to express the firefly luciferase reporter gene from the Cytomegalovirus (CMV) LTR promoter (Danko, I., Fritz, J. D., Jiao, S., Hogan, K., Latendresse, J. L., and Wolff, J. A. Gene Therapy Pharmacological enhancement of in vivo foreign gene expression in muscle, volume 1, pp. 114–121, 1994; incorporated herein by reference). The plasmid also contains the SV40 intron and poly A addition signals for proper and efficient π. RNA processing. All plasmids were purified by alkaline lysis and then two cesium chloride gradients as previously described (Sambrook, J., Fritsch, E. F., and Maniatis, T. (1989) in Molecular Cloning Cold Spring Harbor Laboratory Press, Cold Spring Harbor, N.Y.; Jiao, S., Williams, P., Beg, R. K., Hodgeman, B. A., Liu, L., Repetto, G., and Wolff, J. A. (1992) Hum. Gene Ther. 3, 21–33; incorporated herein by reference).

3. Preparation of Transfection Complexes

The transfection complexes are prepared by adding the polynucleotide by mixing the said polynucleotide with one or more amphipathic compounds and an effective amount of a polynucleotide binding protein. By "mixing" we mean putting together in a solution of water or a water-miscible solvent such as ethanol in small amounts that is not toxic to cells (Campbell, M J. Lipofection reagents prepared by a simple ethanol injection technique. BioTechniques 1995;18:1027–1032; incorporated herein by reference). In one preferred embodiment, the polynucleotide is mixed first with the DNA-binding protein in serum-free media and then the amphipathic compound is added to the mixture containing the polynucleotide and DNA-binding protein. The mixture containing the ternary complex of polynucletide, DNA-binding protein and amphipathic compound is then added to the cells.

4. Preparation of DNA-binding Protein

A DNA-binding protein is a natural protein, either in its native state or modified. By "natural" we mean that is produced in an organism such as *E. coli* for recombinant proteins or isolated from an animal tissue, such as calf thymus or liver. By "DNA-binding protein" we mean that it associates with DNA under certain conditions and forms a complex with DNA with a high binding constant. In one preferred embodiment, the DNA-binding protein is cationic having a net positive-charge. One preferred type of DNA-binding protein is histone protein which is a group of proteins that form chromatin which is a structure in which DNA is present in living cells. Examples of histone proteins are H1, H2A, H2B, H3 and H4. Histone H1 protein is the preferred histone type. It can be purchased from several company suppliers such as Sigma, Life Technologies, or Boeringer-Manheim Corp. They prepare the histone H1 from tissues such as calf thymus or liver. All of the isolation procedures use the perchloric extraction technique. Column chromatography could be used to prepare the histone H1 also. To those skilled in the art, histone H1 proteins can be recognized in many species in how it is prepared by perchloric acid extraction. Histone H1 also signifies a specific amino acid sequence that is homologous across different species. Histone H1 also refers to its function as a linker chromatin protein which means that it cross-links DNA as it enters and leaves nucleosomes which are parts of chromatin.

In another embodiment, the DNA-binding protein is H2A or H2B which can be purchased from several suppliers such as Sigma, Life Technologies, or Boeringer-Manheim Corp. They are best prepared by ion exchange chromatography. H2A or H2B proteins can also be recognized by specific amino acid sequences that are homologous across different species. The histone H2A and H2B proteins are included in nucleosomes. The histone H1 protein can also be produced in bacteria using standard recombinant DNA technology. This enables the histone H1 to be easily modified or combined with other protein or peptide parts. In one preferred embodiment the recombinant DNA-binding protein, NLS-H1, was prepared using the pET bacterial expression system (Novagene, Madison, Wis.) (Studier, F. W., Rosenberg, A. H., Dunn, J. J., and Dubendorff, J. W. (1990) methods Enzymol. 185, 60–89; incorporated herein by reference). The coding sequence of the nuclear localizing signal from the SV40 large T antigen (amino acid residues PKKKRKVEDK, Kalderon, D., Roberts, B. L., Richardson, W. D., and Smith, A. E. (1984) Cell 39, 499–509; incorporated herein by reference) was linked to the sequence for the C-terminal domain of human histone H1 ) (amino acid residues 99–193, Doenecke, D., and Tonjes, R. (1986) J. Mol. Biol. 187, 461–464; incorporated herein b reference) using polymerase chain reaction (PCR). The 5' primer contained nucleotides encoding the NLS sequence, and both primers contained restriction sites for cloning the PCR product into the NdeI/BamHI sites of pET16b (Novagene, Madison, Wis.) and nucleotides which complemented the sequence corresponding to the 7 amino acids at each end of the histone H1C-terminal domain. Following amplification of the desired region of DNA from genomic DNA (isolated from human peripheral blood, gift of R. Gregg), the amplified product was reacted with NdeI and BamHI restriction endonucleases (New England Biolabs, Boston, Mass.) and ligated into pET16b. The resulting pDNA, pET16b-NLS-H1, was verified by sequence analysis and transformed into E. coli BL21(DE3) (Novagene). The approximate 16kDa NLS-H1protein was induced by adding IPTG to the growth medium to a final concentration of 1mM. The induced protein was solubilized in 7 M guanidinium hydrochloride dissolved in bind buffer (5 mM imidazole, 500 mM NaCl, 20 mM Tris-HCl, pH 7.9). Following renaturation in 10 volumes of bind buffer, the NLS-H1 protein was purified by Ni++ affinity chromatography (NTA-agarose, Qiagen, Chatsworth, Calif.). Fractions containing NLS-H1 were dialyzed against Hepes Buffered Saline (HBS as defined in Sambrook, J., Fritsch, E. F., and Maniatis, T. (1989) Molecular Cloning Cold Spring Harbor Laboratory Press, Cold Spring Harbor, N.Y.). Protein concentration was determined using the BCA protein assay (Pierce, Rockford, Ill.) and purity was analyzed by sodium-dodecyl-sulfate polyacrylamide gel electrophoresis (15% polyacrylamide) as previously described (Fritz, J. D., Swartz, D. L., and Greaser, M. L. (1989) Anal. Biochem. 180, 205–210).

5. Preparation of Amiphipathic Compounds

An amphipathic compound has both hydrophilic (water-soluble) and hydrophobic (water insoluble) parts. In one preferred embodiment the amphipathic compounds constitute a liposome which are vesicles that contain one or more bilayers with an internal aqueous compartment. To those skilled in the art, liposomes can be prepared by a variety of techniques. The liposomes were prepared by mixing chloroform solutions of the different lipids in 1.5-ml microcentrifuge tubes (Fisher) with screw caps and removing the chloroform in a SpeedVac SCV100 (Savante, Humble, Tex.) to produce dried lipid film. Tubes were placed under vacuum overnight to remove solvent traces. The amounts of cationic lipids in all preparations were 1.34 umol/ml with different amounts of other lipids as specified. One ml of sterile 10 mM HEPES pH 7.8 was added, vortexed for 1 min at room temperature and then sonicated in bath sonicator (Branson 2200) to obtain a clear emulsion. DOPE (Sigma or Avanti, Alabaster, Ala.) was included in some of the liposomes.

In one preferred embodiment the liposome is non-cationic which means that its net charge is neutral or negatively charged. It can be prepared using dioleoylphosphatidyl ethanolamine (DOPE) alone or combined with other lipids such as dioleoylphosphatidyl serine (DOPS) or oleic acid.

In another embodiment, the liposome is cationic which means that its net charge is positively-charged. These include cationic liposomes that can be purchased from commercial suppliers such as Lipofectin (Life Technologies, Bethesda, Md.), LipofectAMINE (Life Technologies), DOTMA (Boeringer-Manheim Corp.) or TansfectACE (Promega Co., Madison, Wis.).

In yet another embodiment, the amphipathic compound contains one or more cationic amphipathic compounds. These cationic amphipathic compounds can be non-natural polyamines wherein one or more of the amines is bound to at least one hydrophobic moiety wherein the hydrophobic moiety is from a group of compounds having a polar first end and a hydrophobic second end, for example: C6–C24 alkane, C6–C24 alkene, sterol, steroid, lipid, fatty acid and hydrophobic hormone. Examples of non-natural polyamine wherein one or more of the amines is bound to at least one hydrophobic moiety include compounds #4, #11, #16, #17, #20, #21, #23, #30, and #32. These non-natural polyamines are incorporated into liposomes either by themselves or combined with DOPE. In one preferred embodiment, the ternary complexes were formed by first mixing 3ug of luciferase plasmid DNA and 6.0 ug histone H1 (Sigma) in serum free medium (10 minutes room temperature) at a 1:2.0 wt:wt ratio in a final volume of at least 150 ul. Cationic lipsomes were then added to generate a final DNA:histone-:liposome ratio of 1:2.0:0.2–1.5 and incubated at room temperature for an additional 10 minutes. This pDNA:histone H1:cationic liposome ratio yielded a positively charged overall complex.

6. Exposure of Cells to Transfection Complexes

Before transfection, the cells are washed once with 2 ml Opti-MEM (Life Technologies Inc.) followed by the addition of 2 ml to each well. Transfection competent complexes were formed using 3 ug of plasmid DNA (encoding luciferase) in a total volume of 150 ul (Opti-MEM+pDNA+ liposomes). The mixtures were incubated at least 10 min at room temperature prior to being added to the cells in the culture dish. After the cells were incubated at 37 degrees C. in 5% $CO_2$/95% air for four hours, the transfection mixture was removed and replaced with 2 ml of DMEM (Life Technologies Inc.)+10% FCS. The cultures were incubated for 24 to 40 hours until they were harvested for analysis of their reporter gene expression.

For determination of luciferase activity, cells were washed with normal saline and lysed by the addition of 200 ul of lysis buffer (0.1% Triton X-100, 0.1M K-phosphate, 1 mM DTT pH 7.8). 20 ul of the cellular extract was analyzed for luciferase activity as previously reported (Wolff, J. A., Malone, R. W., Williams, P., Chong, W., Acsadi, G., Jani, A. and Felgner, P. L. Direct gene transfer into mouse muscle in vivo. Science, 1465–1468, 1990). The amount of soluble protein in extracts was determined by the BIO-RAD Protein Assay Reagent (Bio-Rad Laboratories, Hercules, Calif.) assay using 15 ul of extract.

SYNTHESIS OF NEW COMPOUNDS

All solvents and reagents were purchased from Aldrich unless otherwise specified.

Compound #4

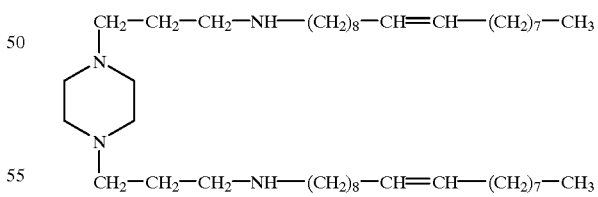

The intermediate for this compound was synthesized as previously described in U.S. patent applications Ser. Nos. 08/365,841 and 08/368,150; incorporated herein by reference. Briefly, 200 mg (1 mmol) of 1,4-Bis(3-Aminopropyl) piperazine was dissolved in 5 ml of dioxane and mixed with 722 mg (2.2 mmol) of oleoyl chloride. The reaction mixture was stirred 16 hours at 70 C. and dioxane was evaporated under vacuum. The residue was dissolved in the mixture of dichloromethane and methanol (ratio 2/1) and dichloromethane was slowly evaporated under reduced pressure in the rotary evaporator. The intermediate compound was crystallized with a yield of 634 mg (87% of the theor.) and a melting point of 224+1 C. TLC on Koeselgel 60F254 plates from EM-Science (Fort Washington, Pa.) using dichloroemthane/methanol ratio 9/1 showed Rf of 0.30 and using dichloromethane/methanol ratio 8/2 was 0.62. 319 mg of the intermediate (0.45 mmol) was dissolved in 2 ml tetrahydrofurane (THF). LialH$_4$ (171 mg (4.5 mmol) was mixed in 6 ml of THF. The solution of the intermediate was slowly added to a stirred solution of LiAlH$_4$. After the addition, the reaction mixture was stirred for 72 hours at 55 C. The mixture was treated with ethyl acetate (1 ml) and 1 N NaOH (0.8 ml) and then filtered. The precipitate was washed two times with 2 ml of THF. The filtrate and washings of the precipitate were dried (MgSO4) and evaporated. The yield was 216 mg (70%). Rf was 0.575 on TLC on cellulose polygram cell 300 (Brickmann Instruments, Inc., Westbury, N.Y.) in ethanol/water/HCl (100:60:2). Proton NMR (in CDCl$_3$) delta 0.85 (6H), 1.25 (48H), 1.4 (2H), 1.65 (4H), 2.0 (8H), 2.35 (8H), 2.45 (4H), 2.60 (8H), 5.35 (4H).

Compound 7

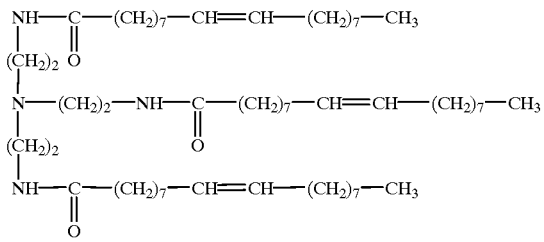

150 ul (1 mmol) Tris (2-aminoethyl)amine was dissolved in 5 ml of dioxane with 400 mg of N,N-diisopropylethylamine and mixed with 1080 mg (3.3 mmol) of oleoyl chloride. The reaction mixture was stirred 16 hours at 70 C. The precipitate was discarded and the solution was cooled. After cooling a precipitate formed which was collected and recrystallized two times from dioxane. (The yield was 370 mg (57%). Rf was 0.8 on TLC on Silica Gel 60 F254 (Alltech, Deefield, Ill.) in chloroform/methanol (3:0.5). Proton NMR (in CDCl$_3$) delta 0.85 (9H), 1.25 (66H), 2.00 (12H), 2.25 (6H), 3.35 (6H), 3.65 (6H), 5.35 (6H), 7.62 (3H).

Compound 11

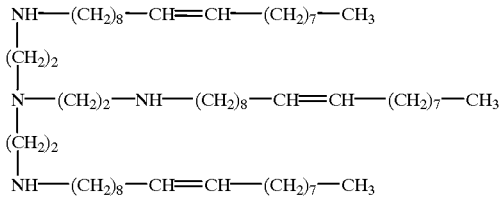

214 mg of compound 7 (0.3 mmol) was dissolved in 2 ml of THF (tetrahydrofuran) and slowly added to a stirred solution of 171 mg of LiAlH$_4$ (4.5 mmol) in 6 ml of THF. The reaction mixture was stirred for 72 hours at 55 C. Then the mixture was treated with ethyl acetate (1 ml) and 1 N NaOH (0.8 ml) and then filtered. The precipitate was washed two times with 2 ml of THF. The filtrate and washings of the precipitate were dried (MgSO$_4$) and evaporated. The yield was 200 mg (75%). Rf was 0.57 on TLC on cellulose polygram cell 300 (Brinkmann Instruments, Inc.) in ethanol/water/HCl (100:60:2). Proton NMR (in CDCl$_3$) delta 0.85 (9H), 1.25 (72H), 1.9 (3H), 2.00 (12H), 2.95 (12H), 3.25 (6H), 5.35 (6H).

Compound 13

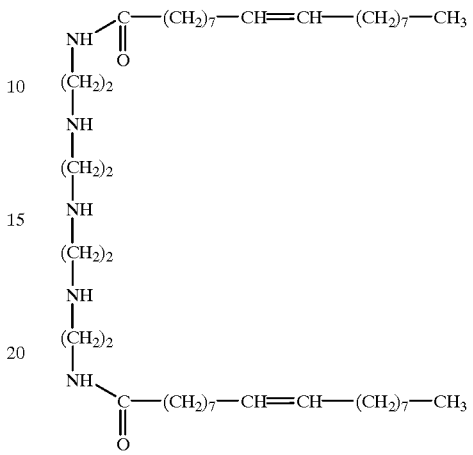

190 ul (1 mmol) tetraethylenepentamine was dissolved in 6 ml of dioxane with 349 ml (2 mmol) of N,N-diisopropylethylamine and mixed with 662 ul (2 mmol) of oleoyl chloride. The reaction mixture was stirred 16 hours at 56 C. and dioxane was evaporated under vacuum. The residue was dissolved in chloroform and applied to a silica gel column. The column was washed with chloroform and the product was eluted by chloroform/methanol (96:4) and the solvent was evaporated. The yield was 150 mg (21%). Rf was 0.8 on TLC on Silica Gel 60 F254 (Alltech) in chloroform/methanol (3:0.5). Proton NMR (in CDCl$_3$) delta 0.85 (6H), 1.28 (44H), 1.75 (3H), 2.00 (8H), 2.25 (4H), 2.50 (8H), 3.4 (4H), 5.35 (4H), 6.50 (2H).

Compound 15

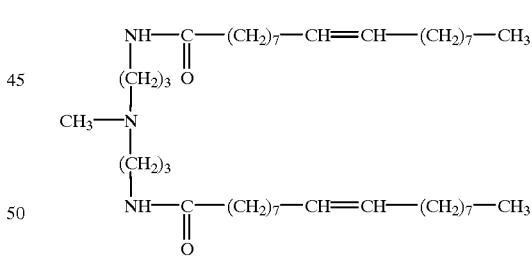

150 mg (1 mmol) of 3,3'diamino-N-methyldipropylamine was dissolved in 10 ml of dioxane and mixed with 722 mg (2.2 mmol) of oleoyl chloride. The reaction mixture was stirred 16 hours at 70 C and dioxane was evaporated under vacuum. The residue was dissolved in chloroform and applied to a silica gel column. The column was washed with chloroform and the product was eluted by chloroform/methanol (96:4) and the solvent was evaporated. The yield was 240 mg (33%.) Rf was 0.5 on TLC on Silica Gel 60 F254 (Alltech) on chloroform/methanol (3:0.5). Proton NMR (in CDCl$_3$) delta 0.85 (6H), 1.25 (44H), 1.6 (4H), 2.00 (8H), 2.18 (4H), 2.65 (3H), 2.92 (4H), 3.4 (4H), 5.35 (4H), 6.75 (2H).

Compound 16

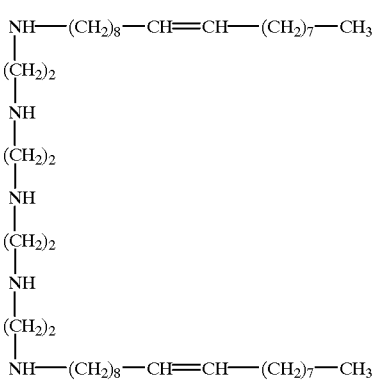

95 mg compound 13 ().13 mmol) was dissolved in 1.4 ml of THF (Tetrahydrofuran) and slowly added to a stirred solution of 100 mg of LiAlH$_4$ (2.6 mmol) in 5 ml of THF. The reaction mixture was stirred for 72 hours at 55 C. Then the mixture was treated with ethyl acetate 1 ml) and 1 N NaOH (0.8 ml) and then filtered. The precipitate was washed two times with 2 ml of THF. The filtrate and washings of the precipitate were dried (MgSO$_4$) and evaporated. The yield was 99 mg (88%(. Rf was 0.55 on TLC on cellulose polygram cell 300 (Brinkmann Instruments, Inc.) in ethanol/water/HCl (100:60:2). Proton NMR (in CDCl$_3$) delta 0.88 (6H), 1.25 (48H), 2.00 (8H), 2.55 (20H), 5.35 (4H).

Compound 17

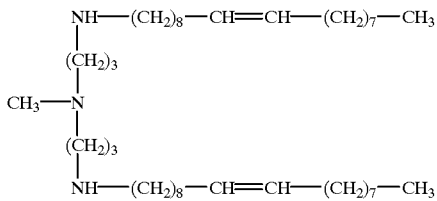

120 mg of compound 15 (0.16 mmol) was dissolved in 2 ml of THF (tetrahydrofuran) and slowly added to a stirred solution of 171 mg of LiAlH$_4$ (4.5 mmol) in 6 ml of THF. The reaction mixture was stirred for 72 hours at 55 C. Then the mixture was treated with ethyl acetate (1 ml) and 1 N NaOH (0.8 ml) and then filtered. The filtrate and washings of the precipitate were dried (MgSO$_4$) and evaporated. The yield was 99 mg (88%). Rf was 0.9 on TLC on cellulose polygram cell 300 (Brinkmann Instruments, Inc.) in ethanol/water/HCl (100:60:2). Proton NMR (in CDCl3) delta 0.9 (6H0, 1.28 (44H), 1.7 (4H), 1.92 (2H), 2.00 (8H), 2.28 (3H), 2.6 (8H), 3.00 (4H), 5.34 (4H).

Compound 18

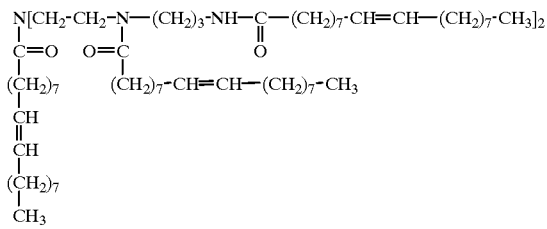

1.046 ml of diisopropylethylamine and 2 ml of oleoyl chloride were added to the solution of 190 ul of tetraethylenepentamine in 10 ml of dimethylformamide. The reaction mixture was stirred at 56 degrees C. for 16 hours. Two layers formed. The upper layer containing the product was collected and washed two-times with 2 ml of dimethylformamide. The residue was dissolved in CHCl$_3$. After column chromatography (eluent:CHCl$_3$/CH$_3$OH— 98:2), 233 mg (16.2% yield) of compound 18 were obtained. Rf was 0.9 using CHCl$_3$/CH$_3$OH— 3:0.6). Proton NMR (in CDCl$_3$) delta 0.88 (15H), 1.27 (110H), 2.01 (20H), 2.25 (10H), 3.44 (16H), 5.34 (10H), 6.37 (2H).

Compound 20

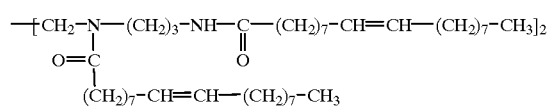

662 ul of oleoyl chloride was added to 184 ul of N,N'-Bis)3-aminopropyl)ethylenediamine (Aldrich) in 8 ml of dioxane. The reaction mixture was stirred for 16 hours at 70 degrees C. The dioxane was evaporated under vacuum, residue was dissolved in 2 ml of chloroform. After silica gel column chromatography (eluent: chloroform/methanol 98:2) 180 mg of #20 were obtained. Yield was 15.4%. Rf was 0.85 on TLC on Silica Gel 60 F254 (Alltech) in chloroform/methanol (3:0.6). Proton NMR (in CDCl$_3$) delta 0.87 (12H), 1.25 (88H), 1.7 (4H), 2.00 (16H), 2.2 (8H), 3.4 (12H), 5.35 (8H), 6.65 (2H).

Compound 21

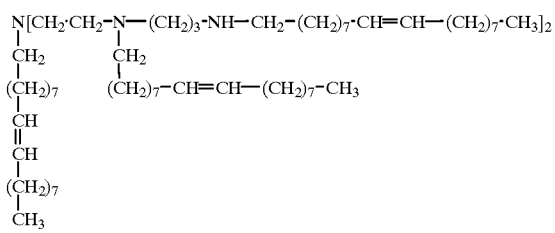

A solution of 233 mg of Compound 18 in 2 ml of THF was added dropwise to a suspension of 310 mg of LiAlH$_4$ in 5 ml of THF. The reaction mixture was treated with 1 ml of ethyl acetate and 1 ml of 1 N NaOH and filtered, washed two times with 2 ml of THF. Filtrate was dried with MgSO$_4$. After column chromatography (eluent: CHCl$_3$/CH$_3$OH— 96:4), 45.9 mg of Compound 21 were obtained (yield= 20.7%). Rf was 0.78 using CHCl$_3$/CH$_3$OH— 3:0.5). Proton NMR (in CDCl$_3$) delta 0.87(15H), 1.3(120H), 2.00 (20H), 2.6(26H), 5.37(10H).

Compound 23

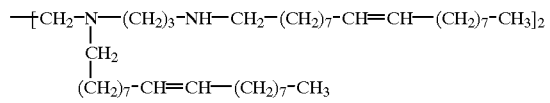

A solution of 180 mg of # 20 in 2 ml of THF was added dropwise to a suspension of 222 mg of LiAlH$_4$ in 5 ml of THF. The reaction mixture was stirred for 96 hours at 56 degrees C. The reaction mixture was treated with 2 ml of ethyl acetate and 2 ml of 1N NaOH. The precipitate was filtered and washed two times with 2 ml of THF. Filtrate was dried using MgSO$_4$. After silica gel column chromatography (eluent: CHCl3: CH3OH 96:4), 13 mg of #23 was obtained. Yield was 7.6%. Rf was 0.7 on TLC on Silica Gel 60 F254 (Alltech) in chloroform/methanol (3:0.5). Proton NMR (in CDCl$_3$) delta 0.87 (12H). 1.25 (96H), 1.87 (2H), 2.00 (16H), 2.50 (4H), 2.8 (20H), 5.38 (8H).

Compound 27

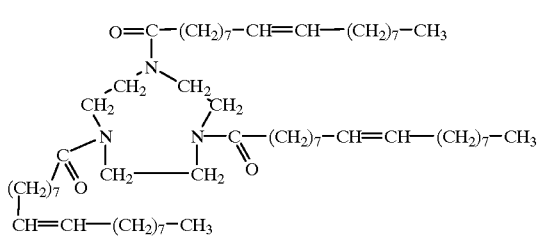

540.5 ul of N,N-diisopropylethylamine and 1.026 ml of oleoyl chloride were added to the solution of 100 mg of 1,4,7,-triazacyclononane (Aldrich) in 5 ml of dioxane. The reaction mixture was stirred for 16 hours at 67 degrees C. A precipitate was formed. The reaction mixture was filtered, dioxane was evaporated, residue was dissolved in 2 ml of chloroform. After silica gel column chromatography (eluent CHCl:CH$_3$OH 98:2) 87 mg of compound #27 were obtained. Yield was 12%. Rf was 0.83 on TLC on Silica Gel 60 F254 (Alltech) in chloroform/methanol (3:0.5). Proton NMR (in CDCl$_3$) delta 0.9 (9H), 1.27 (66H), 2.00 (12H), 2.27 (6H), 3.4 (6H), 3.4 (6H), 3.7 (6H), 3.7 (6H), 5.35 (6H).

Compound 28

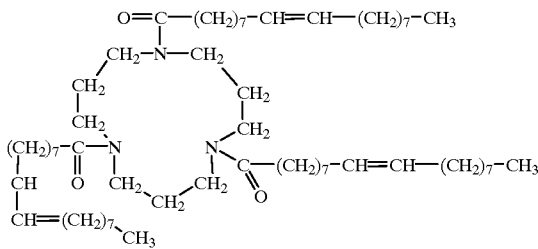

407.5 ul of N,N-diisopropylethylamine and 774 ul of oleoyl chloride were added to the solution of 100 mg of 1,5,9-triazacyclododecane (Aldrich) in 5 ml of dioxane. The reaction mixture was stirred for 16 hours at 67 degrees C. When the reaction mixture was cooled to room temperature, a white precipitate was formed which was filtered. Dioxane was evaporated, residue was dissolved in 2 ml of chloroform. After silica gel column chromatography (eluent CHCl3:CH3OH 98:2) 124.5 mg of # 28 were obtained. Yield was 22%. Rf was 0.8 on TLC on Silica Gel 60 F254 (Alltech) in chloroform/methanol (3:0.4). Proton NMR (in CDCl$_3$) delta 0.9 (9H), 1.3 (66H), 2.00 (12H), 2.3 (6H), 3.42 (12H), 5.35 (6H).

Compound 30

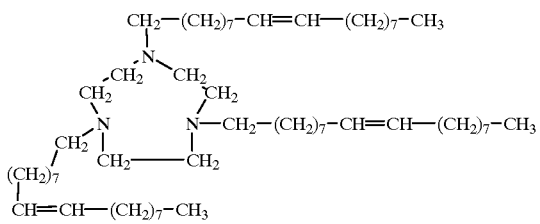

The solution of 77 mg of #27 in 1 ml of THF was added dropwise to a suspension of 98 mg of LiAlH$_4$ in 5 ml of THF. The reaction mixture was stirred for 120 hours at 57 degrees C. The reaction mixture was treated with 1 ml of ethyl acetate and 1 ml of 10% NaOH until a white precipitate was formed. Then it was filtered and washed two times with 2 ml of THF. Filtrate was dried with MgSO$_4$. 56 mg was obtained. Yield was 76%. Rf was 0.65 on TLC on Silica Gel 60 F254 (Alltech) in chloroform/methanol (3:0.6). Proton NMR (in CDCl$_3$) delta 0.9 (9H), 1.25 (66H), 2.00 (12H), 2.75 (6H), 3.7 (12H), 5.35 (6H).

Compound 32

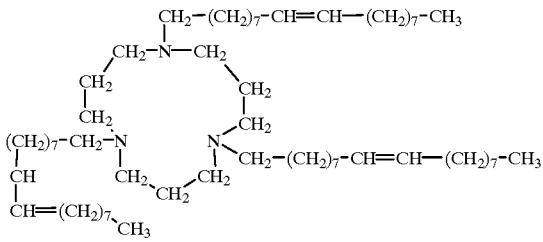

The solution of 97 mg of # 28 in 1.5 ml of THF was added dropwise to a suspension of 178 mg of LiAlH$_4$ in 4 ml of THF. The reaction mixture was stirred for 72 hours at 57 degrees C. The reaction mixture was treated with 1 ml of ethyl acetate and 1 ml of 10% NaOH. Then it was filtered and washed two times with 2 ml of THF. Filtrate was dried using MgSO$_4$. 30 mg was obtained with a yield of 32.3%.

EXAMPLES

The following Examples illustrate preferred embodiments of the present invention and do not limit the specifications and claims in any way.

1. A recombinant human histone H1 protein produced in bacteria binds to plasmid DNA (pDNA).

Methods

NLS-H1 preparation—A recombinant DNA-binding protein, NLS-H1, was prepared using the pET bacterial expression system (Studier, F. W., Rosenberg, A. H., Dunn, J. J., and Dubendorff, J. W. (1990) Methods Enzymol. 185, 60–89). The coding sequence of the nuclear localizing signal from the SV40 large T antigen (amino acid residues PKKKRKVEDK, Kalderon, D., Roberts, B. L., Richardson, W. D., and Smith, A. E. (1984) Cell 39, 499–509) was linked to the sequence for the C-terminal domain of human histone H1 (amino acid residues 99–193, Doenecke, D., and Tonjes, R. (1986) J. Mol. Biol. 187, 461–464) using PCR. The 5' primer contained nucleotides encoding the NLS sequence, and both primers contained restriction sites for cloning the PCR product into the NdeI/BamHI sites of pET16b (Novagene) and nucleotides which complemented the sequence corresponding to the 7 amino acids at each end of the histone H1 C-terminal domain. Following amplifications of the desired region of DNA from genomic DNA (isolated from human peripheral blood, gift of R. Gregg), the amplified product was reacted with NdeI and BamHI restriction endonucleases (New England Biolabs) and ligated into pET16b. The resulting pDNA, pET16-NLS-H1, was verified by sequence analysis and transformed into *E. coli* BL21 (DE3) (Novagene). The approximate 16-kDa NLS-H1 protein was induced by adding IPTG (isopropyl thiogalactopyranoside) to the growth medium to a final concentration of 1 mM. The induced protein was solubilized in 7M guanidinium hydrochloride dissolved in bind buffer (5 mM imidazole, 500 mM NaCl, 20 mM Tris-HCl, pH 7.9). Following renaturation in 10 volumes of bind buffer, the NLS-H1 protein was purified by Ni++ affinity chromatography (NTA-agarose, Ciagene). Fractions containing NLS-H1 were dialyzed against Hepes Buffered Saline (HBS). Protein concentration was determined using the BCA protein assay (Pierce) and purity was analyzed by sodium-dodecyl-sulfate polyacrylamide gel electrophoresis (15% polyacrylamide) as previously described (Fritz, J. D., Swartz, D. L., and Greaser, M. L. (1989) Anal. Biochem. 180, 205–210).

Poly-L-lysine (hydrochloride, 15–30–kDa range), calf thymus histones types V-S, VII-S and VIII-S were obtained from Sigma. Calf thymus histone type V-S contains predominantly histone H1. Calf thymus histone type VII-S contains predominantly histones H2A and H2B. Calf thymus histone type VIII-S contains predominantly histones H3 and H4. The type V-S, VII-S and VIII-S histones will here after be referred to as histone H1, histone H2A/H2B and histone H3/H4, respectively. Protamine was obtained from Elkins-Sinn Incorporated.

Electron microscopy—Protein-pDNA complexes were prepared in HBS 30 min before application to polylysine-carbon coated grids. Sample preparation and examination was done as previously described (Dowty, M. E., Gurevich, V., Berg, R. K., Repetto, G., and Wolff, J. A. (1992) Methods Mol. Cell. Biol. 3, 167–174).

DNA binding assay—Agarose gel electrophoresis was used to determine the ability of the various proteins to bind pDNA. All gels were stained with ethidium bromide following electrophoresis.

Results

Binding of NLS-H1 to pDNA—Migration of pDNA (plasmid DNA) in agarose gels was altered by the addition of NLS-H1. Plasmid DNA containing no NLS-H1 had the expected migration of both supercoiled and open circular forms. The addition of 0.16 mg NLS-H1/mg pDNA resulted in the appearance of a band slightly above the supercoiled band, and prevented some pDNA from migrating into the gel. No difference in the intensity or migration of the open circular pDNA form was observed. At 0.4 mg NLS-H1/mg pDNA, the supercoiled band migration was further retarded, and a large amount of material remained in the sample well. The intensity of the open circular form of the pDNA was also decreased by the addition of 0.4 mg NLS-H1/mg pDNA. At 0.8–1.6 mg NLS-H1/mg pDNA, both supercoiled and open circular bands no longer migrated int the gel and the only visible material was at the sample well. Similar gel retardation patterns were obtained for pDNA complexes made with calf thymus histone H1, H2A/B, H3/H4, poly-L-lysine, or protamine and the amounts required to obtain plasmid migration patterns similar to those obtained for 0.4 mg NLS-H1/mg pDNA complexes were 1.05, 1.8, 4.5, 0.65, or 0.6 mg/mg pDNA, respectively.

EM studies were conducted to study binding of NLS-H1 to pDNA as well. Plasmid DNA was predominantly supercoiled prior to NLS-H1 binding but open circular forms were also observed. After NLS-H1 binding, the pDNA appeared condensed and rod-like. These rod shaped structures could be observed at concentrations as low as 0.16 mg NLS-H1/mg pDNA, and predominated at 0.4 mg NLS-H1/mg pDNA. Increasing the amount of NLS-H1 resulted in additional compaction of the pDNA, and also the formation of large aggregates. Samples containing 1.6 mg NLS-H1/mg pDNA precipitated. Similar structures were observed for complexes studied with calf thymus histone H1 and poly-L-lysine but the poly-L-lysine complexes tended to aggregate more readily.

Discussion

The extent of pDNA binding by the basic proteins was determined by agarose gel electrophoresis and EM studies. Addition of approximately 125 NLS-H1 molecules/pDNA molecule (0.4 mg NLS-H1/mg pBS.RSVLux) substantially reduced the quantity of pDNA entering the agarose gel. This ratio putatively neutralizes about 75% of the pDNA charge based on the number of lysine and arginine residues in NLS-H1. Substantial compaction of pDNA to rod-shaped structures also occurred with 125 NLS-H1 molecules/pDNA molecule. Doubling the molar ratio to 250 NLS-H1/pDNA (0.8 mg NLS-H1/mg pDNA) prevented all of the pDNA from entering the agarose gel and which, as the EM studies indicated, was associated with the formation of large aggregates. Precipitation of the pDNA from solution occurred at 500 NLS-H1 molecules/pDNA molecule (1.6 mg NLS-H1/mg pDNA). These results suggest that NLS-H1 binds pDNA.

2. The Accessibility of Plasmid DNA within H1/Cationic Lipid Complexes to Ethidium Bromide Methods The complexes were prepared as above using NLS-H1. 5 ul of 0.7 mg/ml of pBS.RSVLux plasmid DNA was mixed with various amounts (indicated in Table below) of Lipofectin (1:1 molar ratio of DOTMA:DOPE sold by Life Technologies-BRL) by adding them to 100 ul of 10 mM Tris, 150 mM NaCl pH 7.5 and incubated 15 min at room temperature. 700 ul of Mg-buffer (10 mM Tris pH 8.5, 0.1 mM $MgCl_2$, 0.1 mM $CaCl_2$) were added. The mixture were incubated 10 min. The assay was performed immediately after adding of 100 ul of 50 mM EDTA and 3 ul of 2.5 mM ethidium bromide solution. For control purposes, the fluorescence measurement was repeated after 50 ul of 1% Triton-X-100 was added to the mixtures. All fluorescence measurements were determined using a Spectrophotometer F 3010 (Hitachi). The table shows the accessibility of the DNA to ethidium bromide which was calculated by dividing the amount of fluorescence without Triton-X-100 by the amount of fluorescence with Triton-X-100.

Results

TABLE

The accessibility of plasmid DNA complexed with NLS-H1 and Lipofectin.

| Conditions | Fluorescence | | Accessibility (%) |
|---|---|---|---|
| | No Triton-X-100 | With Triton-X-100 | |
| DNA alone | 6.95 | 6.52 | |
| DNA + NLS-H1 | 4.48 | 4.67 | 96 |
| DNA + NLS-H1 + 2 ul Lipofectin | 4.20 | 4.55 | 92 |
| DNA + NLS-H1 + 4 ul Lipofectin | 3.34 | 4.01 | 83 |
| DNA + NLS-H1 + 6 ul Lipofectin | 2.85 | 3.90 | 73 |
| DNA + NLS-H1 + 8 ul Lipofectin | 2.45 | 3.45 | 70 |

Discussion

These results demonstrate that the majority of the plasmid DNA within NLS-H1/Lipofectin ternary complexes are accessible to ethidium bromide. Several publications have demonstrated that the majority of the plasmid DNA within binary complexes containing only DNA and Lipofectin is not accessible to interaction with ethidium bromide.

3. Histone and Commercially-Available Cationic Lipids

Methods

Cell Culture—NIH 3T3, COS-7, HeLa, and 293 cells were cultured in D-MEM (GIBCO-BRL) supplemented with 10% fetal Bovine Serum (Hyclone). All cultures were maintained in a humidified atmosphere of 5% CO2 in air at 37 degrees C.

Transfections—Transfections requiring only pDNA and lipofectin (GIBCO BRL also known as Life Technologies, Bethesda, Md.), lipofectAMINE (GIBCO BRL), lipofectACE (GIBCO BRL ) or DOTAP (Boehringer Mannheim) were prepared according to the manufacturers' recommendations. Transfections requiring the addition of DNA-binding proteins had the particular protein added to the DNA 10 min prior to the addition of cationic liposomes. All complexes were prepared in 0.2 ml of serum-free Opti-MEM I Reduced-Serum Medium (GIBCO BRL).

Cells were plated in 35 mm wells of 6-well tissue culture dishes and transfected when subconfluent (40–60%). The cells were first rinsed with Opti-MEM I Reduced-Serum Medium and fresh Opti-MEM I Reduced-Serum Medium was added to each well (1.8 ml) followed by the transfection complexes. The transfection solution was removed after 4 h and replaced with fresh growth media. Cells were assayed for gene expression 24–36 h after transfection and total protein was also measured on a replicate plate using the BCA assay.

All transfections were performed in duplicate and then repeated on at least three separate occasions. Data presented represent results observed for all three trials but are from a single transfection experiment.

The plasmid pBS.RSVLux (Danko, I., Fritz, J. D., Jiao, S., Hogan, K., Latendresse, J. L., and Wolff, J. A. (1994) Gene Therapy 1, 114–121; incorporated herein by reference) expresses firefly luciferase from the Rous sarcoma virus (RSV) promoter and contains the SV40 intron and polyA addition sequences within pBluescript KS- (Stratagene, La Jolla, Calif.). Similarly, PBS.CMVLacZ was derived from pCMVb-gal (Jiao, S., Cheng, L., Wolff, J. A., and Yang, N. S. (1993) Bio/technology 11, 497–502) by placing the CMV promoter, b-galactosidase coding sequence and the SV40 intron/poly A sequences within pBluescript KS-. The plasmid pSV2Neo expresses the neomycin-resistance gene from the SV40 early promoter. All plasmids were purified using two cesium chloride gradients as previously described (Jiao. S., Williams, P., Berg, R. K., Hodgeman, B. A., Liu, L., Repetto, G., and Wolff, J. A. (1992) Hum. Gene Ther. 3, 21–33; incorporated herein by reference). Cells were transfected with 5 ug of pDNA. Luciferase and B-galactosidase assays were performed as previously described (de Wet, J. R., Wood, K. V., DeLuca, M., Helinski, D. R., and Subramani, S. (1987) Mol. Cell. Biol. 7, 725–737; Price, J., Turner, D., and Cepko, C. (1987) Proc. Natl. Acad. Sci. U.S.A. 84, 156–160; incorporated herein by reference).

Results

TABLE

The use of histone proteins substantially increase the transfection efficiency of lipofectin in COS-7 cells.

| Complex Type | Luciferase Activity ($\times 10^6$ light units/mg cell protein) |
|---|---|
| 3.0 µg lipofectin/µg pDNA | 37.8 |
| 0.4 µg NLS-H1 + 0.375 µg | 1,740 |

TABLE-continued

The use of histone proteins substantially increase the transfection efficiency of lipofectin in COS-7 cells.

| Complex Type | Luciferase Activity ($\times 10^6$ light units/mg cell protein) |
|---|---|
| lipofectin/µg pDNA | |
| 0.7 µg calf thymus histone H1 + 0.75 µg lipofectin/µg pDNA | 1,480 |
| 1.35 µg calf thymus histone H2A/B + 0.75 µg lipofectin/µg pDNA | 348 |
| 4.95 µg calf thymus histone H3/H4 + 0.75 µg lipofectin/µg pDNA | 2.7 |
| 1.0 µg poly-L-lysine + 3.0 µg lipofectin/µg pDNA | 126 |
| 0.3 µg protainine + 0.75 µg lipofectin/µg pDNA | 26 |

In the COS cell results shown above, the highest levels of luciferase expression were observed in cells transfected with complexes containing either NLS-H1 or calf thymus histone H1 ($1.74 \times 10^9$ and $1.48 \times 10^9$, respectively). Similar results were also obtained in 3T3 cells. In 3T3 cells transfected with the ternary complexes luciferase activity was $1-5 \times 10^6$ L.U. when lipofectin was used alone as compared to $1.00 \times 10^8$ and $6.25 \times 10^7$ when lipofectin was used with NLS-H-1 or calf thymus histone H1, respectively. The luciferase activity was at least 45 times higher in COS7 cells and at least 20 times in NIH 3T3 cells transfected with ternary NLS-H1-pDNA-lipofectin complexes compared to binary pDNA-lipofectin complexes.

Ternary NLS-H1-pDNA-lipofectin complexes also required much less lipofectin than binary pDNA-lipofectin complexes (0.375 verses 3.0 µg lipofectin/µg pDNA). The use of 0.16–0.8 µg NLS-H1/µg pDNA with 3 µg of lipofectin/µg pDNA increased luciferase activity approximately 3-fold. Luciferase activity observed in cells transfected with protein free-pDNA-lipofectin complexes containing 1.5 µg or less of lipofectin/µg pDNA was at most 1/10 of that observed for protein free pDNA-lipofectin complexes containing the optimal amount of lipofectin (3.0 µg lipofectin/µg pDNA).

Similar increases in luciferase activity were obtained in both 293 or HeLa cells transfected with pDNA-protein-lipofectin complexes compared to those lacking protein. Cells transfected with NLS-H1-pDNA-lipofectAMINE complexes had luciferase activity levels (light units/mg cell protein) at least twice that obtained with pDNA-lipofectAMINE complexes ($2.2 \times 10^9$ verses $7.96 \times 10^8$ in COS-7 cells and $1.84 \times 10^9$ verses $7.7 \times 10^8$ in NIH 3T3 cells). Transfection with complexes comprised of 0.4 µg NLS-H1+ 3.0 µg lipofectAMINE/mg pDNA had the highest levels of luciferase activity compared to any other transfection complex. Phase contrast microscopy indicated that cells transfected with lipofectAMINE containing complexes had approximately 30% less number of cells following transfection. This reduction in cellular survival was quantified by measuring the total protein at the time of cell harvesting for the luciferase assays. Compared to non-transfected cells the level of protein measured in COS-7 cells transfected with lipofectAMINE containing complexes (with or without NLS-H1) was 40% less. In comparison, COS-7 cells transfected with pDNA-lipofectin complexes had a 23% decrease in total cell protein and those with NLS-H1-pDNA-lipofectin complexes had a 7% reduction in total cell protein compared to non-transfected cells. Similar decreases (based on total protein measured at the time of luciferase assay) were also observed for NIH 3T3 cells (data not shown). In each of these cases, cells were transfected with complexes which yielded the highest level of luciferase expression.

Studies with DOTAP and lipofectACE showed at least a 2-fold improvement in reporter gene expression in cells transfected with complexes containing either NLS-H1 or calf thymus histone H1 (data not shown).

Transfections using the B-galactosidase reporter gene and optimal NLS-H1-pDNA/lipofectin complexes showed at least 2.5 times more positive B-galactosidase-positive cells compared to samples transfected with optimal pDNA-lipofectin complexes. It was estimated that at least 26% of the NIH 3T3 cells stained positive for B-galactosidase 24 h after transfection with pDNA-NLS-H1-lipofectin complexes compared to at most 10% in samples transfected with pDNA/lipofectin complexes. In COS-7 cells, approximately 30% of the cells stained positive for B-galactosidase in NLS-H-1-pDNA-lipofectin transfected samples compared to at most 9% in pDNA lipofectin transfected samples.

Transfected cells were stained with Hoechst 33258 to visualize DNA and TRITC-labeled concanavalin A to visualize the cell membrane. Less than 10% of the cells six hours after lipofectin-pDNA transfection contained DNA outside the nucleus. At least 50% of the cells contained multiple small DNA containing regions outside the nucleus six hours after NLS-H1-pDNA?/lipofectin transfection. These small circular shaped DNA-containing regions were thought to be the NLS-H1-pDNA-lipofectin complexes. These regions could be seen at multiple focal points throughout the cells and were found only in the area of the sample defined by the cell boarder. Diffuse, cytoplasmic DNA staining was also evident. Cells transfected with complexes lacking pDNA had only nuclear DNA Hoechst staining.

Discussion

Cells transfected with ternary DNA-binding protein-pDNA-lipofectin complexes had substantially increased luciferase and B-galactosidase expression compared to transfections using binary pDNA-lipofectin complexes. The increase in expression was greatest for samples containing NLS-H1 or calf thymus histone H1 or H2A/B. In addition, transfection complexes containing NLS H1 required the least amount of lipofectin (0.375 μg) to obtain optimal levels of gene expression. Histone H1 increased the transfection efficiency of not only lipofectin but also other cationic lipid formulations including DOTAP, lipofectACE, and lipofectAMINE. Furthermore, NLS-H1/pDNA-lipofectin complexes were superior to other transfection complexes examined in this study involving gene transfer into cultured mammalian cells based on the levels of foreign gene expression, reduced cellular toxicity, and the low amount of lipofectin and protein reagents required to prepare these complexes.

The ability to produce a recombinant DNA-binding protein may lead to alternative approaches in receptor-mediated gene transfer techniques. Currently, receptor-mediated gene transfer techniques rely upon chemical cross-linking to attach the desired ligand to the DNA-binding protein (Wu, G. Y., and Wu, C. H. (1988) J. Biol. Chem. 263, 14621–14624; Wagner, E., Zenke, M., Cotten, M., Beug, H., and Birnstiel, M. L. (1990) Proc. Natl. Acad. Sci. U.S.A. 87, 3410–3414). In the case of peptide derived ligands, it should now be possible to produce an entirely recombinant molecule which avoids chemical cross-linking strategies and can easily be purified.

In summary, NLS-H1-pDNA-lipofectin complexes gave superior gene transfer compared to the other complexes studied. These complexes used the least amount of protein and cationic liposome reagent, and transferred reporter genes to greater numbers of cells with lower cytotoxicity than complexes containing lipofectAMINE. The availability and simplicity in using these reagents provides a rapid and inexpensive means to greatly enhance cationic lipid-mediated gene transfer.

4. Histone H1 and Amphipathic Compounds

Methods

Complex formation—Ternary complexes were formed by first mixing 3 μg of luciferase plasmid DNA and 6.0 μg histone H1 (Sigma) in serum free medium (10 minutes room temperature) at a 1:2.0 wt:wt ratio in a final volume of at least 150 μl. Cationic liposomes were then added to generate a final DNA:histone:liposome ratio of 1:2.0:0.2–1.5 and incubated at room temperature for an additional 10 minutes. This pDNA:histone H1:cationic liposome ratio yielded a positively charged overall complex.

The liposomes were prepared by mixing chloroform solutions of the different lipids in 1.5 ml microcentrifuge tubes (Fisher) with screw caps and removing the chloroform in a SpeedVac SVC100 (Savant) to produce dried lipid films. Tubes were placed under vacuum overnight to remove solvent traces. The amounts of cationic lipids in all preparations were 1.34 μmol/ml with different amounts of other lipids as specified. One ml of sterile 10 mM HEPES buffer pH 7.8 was added, vortexed for 1 min at room temperature and then sonicated in bath sonicator (Branson 2200) to obtain a clear emulsion.

Transfections—NIH 3T3 cells were grown in Dulbecco's modified Eagle's medium (DMEM) supplemented with 10% fetal calf serum. Prior to transfection, cells were washed 1X in OptiMEM (Gibco-BRL) followed by addition of 2 mls of Opti-MEM to each 35 mm well. Pre-formed ternary complexes (3μg pDNA/well in a 150 μl volume) were then added to each well and dishes were placed at 37 degrees C. in 5% CO2. After a 3–4 hour incubation, complexes were removed and 2 mls fresh growth medium was added. Following a 40–48 hour incubation cells were scraped off the plates and lysed. 10% (20 μl) of the 200 μl cell lysate (total cellular proteins) from each plate was assayed for reporter gene expression (luciferase) and total activity was quantitated.

Results

Table 1 shows the reporter gene expression (luciferase activity) derived from transfections using different cationic lipids with and without histone H1 on NIH 3T3 cells. Each value represents an average of two transfections with the exception of the compound #4 minus H1 value which represents a single transfection.

TABLE

H1 protein substantially increases the transfection efficiency of a variety of novel amphipathic compounds.

| Amphipathic Compound * | Mean Luciferase Activity (L.U. × $10^6$) | | Fold Increase With H1 |
|---|---|---|---|
| | Without H1 | With H1 | |
| #4 (ODAPP) | 1.15 | 18.5 | 16.1 |
| #11 (Tris) | 1.08 | 10.19 | 9.4 |
| #17 (D-ETA) | 0.91 | 7.7 | 8.46 |
| #16 | 0.02 | 5.75 | 287.5 |
| #20 | 0.003 | 2.58 | 860 |
| #20/DOPE (1:1) | 0.004 | 7.46 | 1,865 |
| #21 | 0.001 | 8.80 | 6,288 |
| #21/DOPE (1:1) | 0.001 | 12.4 | 12,441 |
| #23 | 0.008 | 27.9 | 3,444 |
| #23/DOPE (1:1) | 0.121 | 46.1 | 381 |
| #30 | 0.205 | 52.7 | 26 |
| #30/DOPE (1:1) | 0.627 | 14.3 | 23 |

* The compound number refers to the number within this application. Our abbreviation for the compound name is included in parentheses. The compounds were used in liposomes by themselves or combined with equimolar (1:1) concentrations of DOPE (dioleoylphosphatidylethanolamine).

Discussion

These results demonstrate that histone H1 increases the transfection efficiency for a wide variety of amphipathic compounds. Some of the compounds such as #16 are very inefficient without H1 but are very efficient when used in conjunction with H1. Therefore, H1 increases various types of amphipathic compounds and cationic lipids that can be used for DNA transfection.

5. The Inclusion of H1 in Cationic Lipid-DNA complexes substantially reduces their cellular toxicity.

Methods

The transfections were done as described above into 3T3 cells in 35-mm well plates using 3 µg of pCMVLux per well. Two days after transfection, the cells were harvested for luciferase assays (20 µl assayed out of 200 µl cellular extract) and protein determinations (µg/15 µl assayed). LipofectAmine transfections were done using 6 µg of lipofectAmine/µg DNA while the "Compound #4+H1" transfections were done using 2 µg H1 (Sigma)/µg DNA and 0.83 µg Compound #4/µg DNA. Values for luciferase and protein assays were the mean of duplicate plates.

Results

TABLE

Compound #4/H1 Reagent enables high transfection efficiency with minimal cellular toxicity.

| Transfection Reagent | Luciferase Activity (L.U. × $10^6$) | Protein (ug/15 ul) |
|---|---|---|
| LipofectAmine | 12.12 | 2.42 |
| Compound #4 + H1 | 22.09 | 7.07 |

Discussion

LipofectAmine is one of the most efficient transfection reagents that is commercially available. Our novel Compound #4/H1 reagent has greater transfection efficiency and less cellular toxicity than LipofectAmine.

Examples for the Use of Histone Proteins with Neutral and Anionic Lipids

6. Histone H1 Enables Plasmid DNA to be Complexed with Non-Cationic Liposomes

Methods

Principle—Different combinations of DOPE (dioleoylphosphatidyletanolamine) liposomes, histone H1, and plasmid DNA were mixed and then centrifuged in sucrose solutions whose density is higher than free liposomes. Complex formation of the liposome is detected when the complex is pelleted during centrifugation.

Specifics—The liposomes were prepared by mixing chloroform solutions of the different lipids in 1.5 ml microcentrifuge tubes (Fisher) with screw caps and removing the chloroform in a SpeedVac SVC100 (Savant) to produce dried lipid films. Tubes were placed under vacuum overnight to remove solvent traces. The amounts of cationic lipids in all preparations were 1.34 µmol/ml with different amounts of other lipids as specified. One ml of sterile 10 mM HEPES buffer pH 7.8 was added, vortexed for 1 min at room temperature and then sonicated in bath sonicator (Branson 2200) to obtain a clear emulsion. DOPE (Sigma or Avanti) was included in some of the liposomes. 10 µl of liposome formulation containing 2 mg of DOPE and 20 µg of rhodamine isothionate-DOPE (Sigma) was added to 800 µl of 30 mM Tris pH 8.5 in 0.2 M sucrose. This is labeled in the Table below as "DOPE". 5 µl of 1.5 mg/ml of H1 was added to this mixture and incubated for 10 min at room temperature (labeled "DOPE+H1"). 10 µl of 0.37 µg/µl plasmid DNA was added to this "DOPE+H1" mixture and incubated for an additional 10 min (labeled "DOPE+H1+DNA"). The same amount of plasmid DNA was also added to the DOPE mixture that did not contain any H1 (labeled "DOPE+DNA").

The above mixtures was centrifuged 10 min at 15,000 RPM in a microfuge and 780 µl was collected and 780 µl of fresh Tris buffer was added. The mixture was centrifuged again and the precipitate was collected. The fluorescence of the supernatant and precipitate was determined using a Hitachi spectrofluorometer.

Results

TABLE

Histone H1 protein enables complex formation between DOPE liposomes and plasmid DNA at alkaline pH.

| Material Within Complex | Percent Fluorescence | |
|---|---|---|
| Added to Plasmid DNA | Supernatant | Precipitate |
| DOPE | 94 | 6 |
| DOPE + H1 | 41 | 59 |
| DOPE + DNA | 95 | 5 |
| DOPE + H1 + DNA | 15 | 185 |

Discussion

A substantial amount of the DOPE liposomes were precipitated only when the plasmid DNA was added to the liposomes in the presence of H1 protein. Without the H1 protein, a trivial amount of complexes formed between the DNA and liposomes. Similar results were obtained with anionic liposomes containing 10% DOPS (dioleoylphosphatidylserine) and 90% DOPE (data not shown). In addition, when the amount of plasmid DNA was assayed in the precipitate and supernatant, a substantial amount of plasmid DNA was present only in the DOPE+H1+DNA mixture (data not shown). These results demonstrate that histone H1 enables plasmid DNA to be complexed substantially with non-cationic liposomes.

2. Plasmid DNA within the Novel Complexes is Accessible to Ethidium Bromide

Methods

Various amounts (indicated in table below) of DOPE liposomes (2 mg lipid/ml) were added to 100 µl of 30 mM Tris, pH 8.5. Then 4.5 µl of 1 mg/ml of H1 was added and the mixture was incubated 10 min at room temperature. Then 700 µl Mg-buffer (10 mM Tris pH 8.5, 0.1 mM $MgCl_2$, 0.1 mM $CaCl_2$) was added. After 10 min incubation, 5 µl of 0.7 mg/ml of pBS.RSVLux plasmid DNA was added. The mixtures were then incubated 15 min further at room temperature. The assay was performed immediately after adding 100 µl of 50 mM EDTA and 3 µl of 2.5 mM ethidium bromide. For control purposes, the fluorescence measurement was repeated after 50 µl of 1% Triton-X-100 was added to the mixtures. The table shows the accessibility of the DNA to ethidium bromide which was calculated by dividing the amount of fluorescence without Triton-X-100 by the amount of fluorescence with Triton-X-100.

Results

TABLE

The accessibility of plasmid DNA complexed with H1 and DOPE liposomes.

| | Fluorescence | | Accessibility |
|---|---|---|---|
| Conditions | No Triton-X-100 | With Triton-X-100 | (%) |
| DNA alone | 11.97 | 11.07 | |
| DNA + H1 | 7.78 | 7.39 | 105 |
| DNA + H1 + 12 ul DOPE | 7.45 | 7.39 | 101 |
| DNA + H1 + 24 ul DOPE | 7.41 | 7.12 | 104 |

TABLE-continued

The accessibility of plasmid DNA complexed with H1 and DOPE liposomes.

| Conditions | Fluorescence | | Accessibility (%) |
| --- | --- | --- | --- |
| | No Triton-X-100 | With Triton-X-100 | |
| DNA + H1 + 36 ul DOPE | 7.00 | 6.67 | 105 |

Similar results shown below were obtained with DOPE/DOPS liposomes. (DOPS=dioleoylphosphatidylserine.) Various amounts (indicated in table below) of 1 mg lipid/ml of DOPE/DOPS (weight ratio of 9:1 respectively) was added to 800 µl of 10 mM Tris, 150 mM NaCl pH 7.5. Then 4.5 µl of 1 mg/ml of H1 was added and the mixture was incubate 10 min at room temperature. 5 µl of 0.75 mg/ml of pBS.RS-VLux plasmid DNA was added and the mixtures incubated an additional 10 min. The assay was performed immediately after adding 3 µl of 2.5 mM ethidium bromide solution. Then 50 µl of 1% Triton-X-100 was added and the assay was repeated.

TABLE

The accessibility of plasmid DNA complexed with H1 and DOPE/DOPS liposomes.

| Conditions | Fluorescence | | Accessibility (%) |
| --- | --- | --- | --- |
| | No Triton-X-100 | With Triton-X-100 | |
| DNA alone | 9.64 | 8.77 | |
| DNA + H1 | 5.09 | 4.77 | 107 |
| DNA + H1 + 12 ul DOPE | 5.58 | 5.19 | 108 |
| DNA + H1 + 24 ul DOPE | 5.10 | 5.14 | 99 |
| DNA + H1 + 36 ul DOPE | 4.53 | 4.7 | 96 |
| DNA + H1 + 48 ul DOPE | 4.56 | 4.86 | 94 |
| DNA + H1 + 60 ul DOPE | 4.20 | 4.49 | 94 |

Discussion

These results demonstrate that the plasmid DNA within the ternary complexes containing H1 and DOPE or the ternary complexes containing H1 and DOPE/DOPS liposomes are completely accessible to interaction with ethidium bromide. This is in striking contrast to inability of ethidium bromide to interact with plasmid DNA within other types of liposomes. Several published studies have demonstrated that plasmid DNA complexed with cationic lipids such as Lipofectin (BRL) is inaccessible to ethidium bromide.

3. Ternary Complexes of Histones, Liposomes, and Plasmid DNA Efficiently Transfect Cultured Cells (NIH 3T3, HepG2, COS).

Methods

Transfection competent complexes are prepared by first mixing histone H1 with either neutral liposomes containing only dioleoyl phophatidyl ethanolamine (DOPE); negative liposomes containing dioleoyl phosphatidyl serine (DOPS) and DOPE; or pH-sensitive negative liposomes containing DOPE and oleic acid. The initial binary complexes were prepared at a ratio of 12 µg liposomes:1.5 µg histone H1 in 100 µl 30 mM Tris-HC1, pH 8.5 for DOPE liposomes or 100 µl OptiMEM (BRL) for DOPS/DOPE liposomes. After a 10 minute incubation at room temperature supercoiled plasmid DNA (pDNA) in 30mM Tris-HC1 pH 8.5(Opti-MEM for DOPS/DOPE liposomes) is added in a 100 µl volume to form ternary complexes at a final ratio of liposomes:protein:pDNA of 12:1.5:1. These complexes are incubated for an additional 15 minutes at room temperature before being added directly to washed cells (40–60% confluent). For 35 mm plates we add 200 µl of pre-formed complexes to wells containing 1.8 ml of Opti-MEM (Gibco-BRL) and incubate on the cells for 2–4 hours at 37 degrees Celsius. After this incubation, complexes are aspirated off the cells and replaced with growth medium (DMEM+10% fetal calf serum). Cells are harvested and assayed for luciferase activity after 24–72 hours.

The liposomes were prepared by mixing chloroform solutions of the different lipids in 1.5 ml microcentrifuge tubes (Fisher) with screw caps and removing the chloroform in a SpeedVac SVC100 (Savant) to produce dried lipid films. Tubes were placed under vacuum overnight to remove solvent traces. One ml of sterile 10 mM HEPES buffer pH 7.8 was added, vortexed for 1 min at room temperature and then sonicated in bath sonicator (Branson 2200) to obtain a clear emulsion. All lipids such as DOPE were purchased from Avanti or Sigma Co.

Results

TABLE

Mean luciferase expression following transfection of 3T3 cells using 3 ug pRSVLux complexed with H1 histone and liposomal complexes.

| Materials Complexed with 3 ug of pRSVLux | Luciferase Activity ($\times 10^3$) Light Units in 20 ul of 200 ul Cellular Extract (n = number or plates) |
| --- | --- |
| 4.5 ug H1 and 12 ug DOPE | 803 (n = 25) |
| 12 ug of liposomes containing DOPS/DOPE (1:9) and 6 ug of H1 | 1,938 (n = 4) |
| 12 ug of liposomes containing oleic acid/DOPE (1:9) and 6 ug of H1 | 410 (n = 2) |
| 12 ug of liposomes containing oleic acid/DOPE (1:9) and 9 ug of H1 | 435 (n = 2) |
| 12 ug DOPE Alone | <20 |
| 6 ug H1 Alone | <20 |
| Lipofectin Alone | 319 (n = 19) |

Similar to cationic liposome/protein/pDNA complexes, ternary complexes consisting of plasmid DNA, H1 and either negatively charged (DOPS/DOPE), neutral (DOPE) or pH-sensitive negatively charged (Oleic acid/DOPE) liposomes can efficiently deliver genes to 3T3 cells (Table above). In agreement with this, HepG2 and COS cells are also efficiently transfected by histone H1/DOPE liposomes with resultant luciferase activities of $2\times10^8$ to $9.5\times10^8$ light units/milligram of total protein.

Discussion

These results show that complexes of plasmid DNA and histone H1 and liposomes can transfect a variety of cultured cells with a substantial amount of transfection efficiency. These liposomes can either be negatively-charged (DOPS/DOPE), pH-sensitive negatively charged (oleic acid/DOPE), or neutral (DOPE alone).

The benefit of the histone-based component liposomal system lies in its inherent flexibility with regard to assembling a wide variety of complexes by changing only one component. Up until now, only cationic liposomes could be used to package DNA into complexes quickly and efficiently. We now present evidence that pDNA/H1 can form transfection competent complexes with pH sensitive, anionic, and cationic liposomes. Thus a wide range of very different liposomes can be incorporated into these ternary complexes and tested for transfection capabilities both in vitro and in vivo.

Futhermore, up to now it was believed that plasmid DNA had to be within liposomes in order to be efficiently transfected. From a simplistic standpoint, it is easy to visualize that once DNA is encapsulated within the aqueous environment of a liposome, a fusion event with either the plasma membrane or an internal endosome would allow the aqueous contents to be extruded into the cytoplasm. Thus it was unexpected when we found that the pDNA was on the outside of transfection competent ternary complexes consisting of liposomes, DNA-binding protein, and pDNA. If the DNA is associated with the outside of a liposome, it is unclear how it would access the cytoplasm even after a liposome-mediated fusion event.

We claim:

1. A compound having the structure:

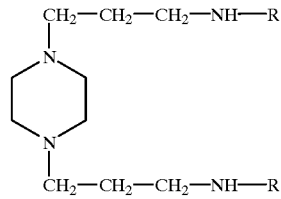

wherein R is the hydrophobic moiety selected from the group consisting of a C12–C20 alkane, C12–C20 alkene, and a C4–C45 lipid.

2. A compound having the structure:

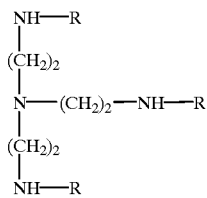

wherein R is the hydrophobic moiety selected from the group consisting of a C14–C24 alkane, C14–C24 alkene, and a C4–C45 lipid.

3. A compound having the structure:

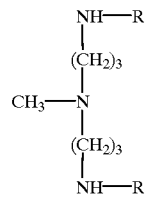

wherein R is the hydrophobic moiety selected from the group consisting of a C6–C24 alkane, C6–C24 alkene, and a C4–C45 lipid.

4. A compound having the structure:

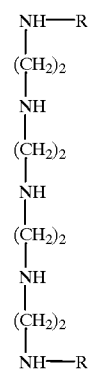

wherein R is the hydrophobic moiety selected from the group consisting of a C12–C24 alkane, C12–C24 alkene, and a C4–C5 lipid.

5. A compound having the structure:

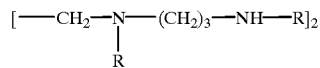

wherein R is the hydrophobic moiety selected from the group consisting of a C14–C24 alkane, C14–C24 alkene, and a C4–C40 lipid.

6. A compound having the structure:

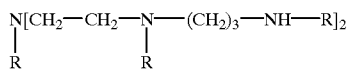

wherein R is the hydrophobic moiety selected from the group consisting of a C6–C24 alkane, C6–C24 alkene, and a C4–C45 lipid.

7. A compound having the structure:

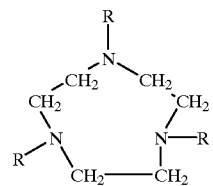

wherein R is the hydrophobic moiety selected from the group consisting of a C12–C24 alkane, C12–C24 alkene, and a C4–C45 lipid.

8. A compound having the structure:

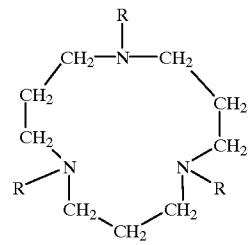

wherein R is the hydrophobic moiety selected from the group consisting of a C6–C24 alkane, and a C4–C45 lipid.

* * * * *